United States Patent
Fan et al.

(10) Patent No.: US 12,157,900 B2
(45) Date of Patent: Dec. 3, 2024

(54) METHOD FOR INDUCING DIFFERENTIATION INTO FUNCTIONAL CEREBRAL CORTICAL CELLS

(71) Applicant: ZHEJIANG HUODE BIOENGINEERING COMPANY LIMITED, Hangzhou (CN)

(72) Inventors: Jing Fan, Hangzhou (CN); Anxin Wang, Hangzhou (CN); Tan Zou, Hangzhou (CN)

(73) Assignee: ZHEJIANG HUODE BIOENGINEERING COMPANY LIMITED, Hangzhou (CN)

(*) Notice: Subject to any disclaimer, the term of this patent is extended or adjusted under 35 U.S.C. 154(b) by 799 days.

(21) Appl. No.: 17/044,916

(22) PCT Filed: Apr. 3, 2019

(86) PCT No.: PCT/CN2019/081156
§ 371 (c)(1),
(2) Date: Oct. 2, 2020

(87) PCT Pub. No.: WO2019/192504
PCT Pub. Date: Oct. 10, 2019

(65) Prior Publication Data
US 2021/0163885 A1    Jun. 3, 2021

(30) Foreign Application Priority Data
Apr. 4, 2018 (CN) .......................... 201810298488.9

(51) Int. Cl.
*C12N 5/079* (2010.01)
(52) U.S. Cl.
CPC ........ *C12N 5/0618* (2013.01); *C12N 2500/34* (2013.01); *C12N 2501/01* (2013.01); *C12N 2501/13* (2013.01)
(58) Field of Classification Search
CPC .......................... C12N 5/0618; C12N 250/34; C12N 2501/01; C12N 2501/13
See application file for complete search history.

(56) References Cited

U.S. PATENT DOCUMENTS

| 2016/0177260 A1* | 6/2016 | Shoji et al. ........... C12N 5/0793 |
| 2018/0010092 A1 | 1/2018 | Dai et al. |
| 2018/0051250 A1 | 2/2018 | Matsumoto et al. |

FOREIGN PATENT DOCUMENTS

| CN | 1059273 A | 8/2005 |
| CN | 101243178 A | 8/2008 |
| CN | 101294146 A | 10/2008 |
| CN | 101309682 A | 11/2008 |
| CN | 105658788 A | 6/2016 |
| CN | 108359638 A | 8/2018 |
| EP | 3031908 | 6/2016 |
| JP | 2008278842 | 11/2008 |
| JP | 2008546385 | 12/2008 |
| JP | WO2016159177 | 2/2018 |
| WO | WO2006/134602 A2 | 12/2006 |
| WO | WO2016117139 | 7/2016 |
| WO | WO2017132596 | 8/2017 |

OTHER PUBLICATIONS

Lepski et al., cAMP promotes the differentiation of neural progenitor cells in vitro via modulation of voltage-gated calcium channels, Front. Cell. Neurosci., 7(155): 1-11. (Year: 2013).*
Barili et al., Sensitivity to ageing of the limbic dopaminergic system: a review, Mechanisms of Ageing and Development, 106: 57-92. (Year: 1998).*
Tio et al., Roles of db-cAMP, IBMX and RA in Aspects of Neural Differentiation of Cord Blood Derived Mesenchymal-Like Stem Cells, PLoS One, 5(2): 1-11. (Year: 2010).*
Selleckchem, IBMX, retrieved from internet Jul. 6, 2023. (Year: 2023).*
Buisson et al., The Inhibitory mGluR Agonist, s-4-carboxy-3-hydroxy-phenylglycine Selectively Attenuates NMDA Neurotoxicity and Oxygen-Glucose Deprivation-induced Neuronal Death, *Neuropharmacology*, 1995, vol. 34, pp. 1081-1087.
Xu et al., Cultured networks of excitatory projection neurons and inhibitory interneurons for studying human cortical neurotoxicity, *Sci. Trans. Med.* 2016, vol. 8, p333ra48.
Ladewig et al., Auto-attraction of neural precursors and their neuronal progeny impairs neuronal migration, *Nature Neuroscience* 2014, vol. 17, p. 24-26.
Smith et al., Inhibition of Activin/Nodal signaling promotes specification of human embryonic stem cells into neuroectoderm, *Developmental Biology*, 2008, vol. 313, p. 107-117.
Lancaster et al., "Cerebral organoids model human brain development and microcephaly", *Nature*, 501:373-379 (2013).
Cao et al., "Enhanced derivation of human pluripotent stem cell-derived cortical glutamatergic neurons by a small molecule", *Sci Rep.*, 7(1):3282 (2017).

(Continued)

*Primary Examiner* — Arthur S Leonard
*Assistant Examiner* — Joseph Paul Miano
(74) *Attorney, Agent, or Firm* — FINNEGAN, HENDERSON, FARABOW, GARRETT & DUNNER LLP (57) ABSTRACT

The present disclosure provides a medium and a method for inducing differentiation into functional cerebral cortical cells, wherein the medium comprises a neural medium and a nutritional supplement and the nutritional supplement is selected from a group consisting of SU5402, BIBF1120, IBMX and glucose. The method describes that specific factors such as an inhibitor of FGF signaling pathway, an inhibitor of VEGF signaling pathway and/or an activator of cAMP are added at specific time points during the induced differentiation process to accelerate the differentiation and maturation of the neural cells. Said method can produce stable and healthy neural cells with major functions at about 7 to 14 days after the initiation of the induced differentiation starting from human neural progenitor cells, with reduced manufacturing cost and shortened production time.

15 Claims, 8 Drawing Sheets

(56) References Cited

OTHER PUBLICATIONS

Shi et al., "Directed differentiation of human pluripotent stem cells to cerebral cortex neurons and neural networks", *Nat Protoc.*, 7(10):1836-1846 (2012).
Extended European Search Report for EP19781651.5, dated Apr. 23, 2021.
Dimos et al., Induced Pluripotent Stem Cells Generated from Patients with ALS Can Be Differentiated into Motor Neurons, *Science*, 2008, vol. 321, p. 1218.
International Search Report for International Application No. PCT/CN2019/081156, dated Jul. 5, 2019.
Ladewig et al., "Supplementary Information of 'Auto-Attraction of Neural Precursors and Their Neuronal Progeny Impairs Neuronal Migration'," Nat Neurosci, Nov. 17, 2013 (Epub), 17(1), 7 pages.

* cited by examiner

Comparative example 1      Example 2

METHOD FOR INDUCING DIFFERENTIATION INTO FUNCTIONAL CEREBRAL CORTICAL CELLS

This application is a national stage filing under 35 U.S.C. § 371 of International Application No. PCT/CN2019/081156, filed on Apr. 3, 2019, which claims the benefit of the filing date of Chinese Patent Application No. 201810298488.9, filed on Apr. 4, 2018.

FIELD OF THE INVENTION

The present disclosure relates to the technical field of inducing differentiation into functional cerebral cortical cells, and particularly relates to a method for inducing fast differentiation of human neural stem cells into functional cerebral cortical cells.

BACKGROUND OF THE INVENTION

Since 2008 (Dimos et al., 2008), human neural cells derived from human induced pluripotent stem cells (hiPSC) or human embryonic stem cells (hESC) by in vitro induced differentiation, and their use in neurological disease research, drug screening, neurotoxicity tests, and transplantation studies have been especially popular in scientific research and drug development, with an increasing number of related articles. Although methods of inducing differentiation have been springing up, it remains a great challenge to obtain a neural cell population with compositions and proportion as well as mature functions that are close to the brain.

It usually takes 30 to 60 days to induce differentiation of human neural progenitor cells into mature and functional cerebral cortical cells. Moreover, these differentiated neural cells hardly adapt real neural structures and functions, such as the distribution of neurotransmitter receptors at synapses, as well as spontaneous, strong and frequent excitatory or inhibitory electrophysiological signals. Furthermore, these neural cells cannot be maintained stably and healthily for a long time on multi-well plates for high-throughput drug screening, as they cannot sustain additional medium exchange. Therefore, high throughput applications of these cells in disease research, drug screening and toxicity tests will remain largely limited if a prolonged culture time is required and real maturation cannot be achieved, which greatly affects the representativeness and reliability of the obtained data.

DESCRIPTION OF THE INVENTION

In view of the above, the present disclosure provides a method for inducing differentiation into functional cerebral cortical cells, in which the method of the present disclosure can give rise to stable and healthy neural cells with major functions in a relatively short time.

The present disclosure provides a method for induced differentiation of functional cerebral cortical cells, comprising the following steps:
neural stem cells or neural progenitor cells are plated on a cell culture plate after being dissociated, cultured by using Neural Differentiation Medium A from day 1, and then cultured by using Neural Differentiation Medium B from day 7;
the Neural Differentiation Medium A comprises one or more of retinoic acid, BDNF, GDNF, ascorbic acid, a nutritional supplement, Neurobasal medium, and B-27 Supplement Minus Vitamin A;
the Neural Differentiation Medium B comprises one or more of BDNF, GDNF, ascorbic acid, a nutritional supplement, Neurobasal medium, and B-27 Supplement Minus Vitamin A;
the nutritional supplement comprises one or more of SU5402, BIBF1120, IBMX, and glucose.

In the present disclosure, specific factors such as an inhibitor of FGF signaling pathway, an inhibitor of VEGF signaling pathway, and/or an activator of cAMP, are added at specific time points during the induced differentiation of neural stem cells or neural progenitor cells to various neural cells to accelerate the differentiation and maturation of neural cells, enabling the generation of stable and healthy neural cells with major functions, including excitatory and inhibitory neurons, around 7~14 days after the initiation of the induced differentiation from human neural progenitor, so that human neural cells grown in vitro can be truly used in the fields such as drug screening, with reduced manufacturing cost and shortened production time.

In the present disclosure, the neural stem cells or neural progenitor cells are firstly plated on a cell culture plate after being dissociated. Specifically, the neural stem cells or neural progenitor cells are dissociated by accutase, plated on a poly-D-lysine/laminin-coated plate at a density of $5 \times 10^5$/cm$^2$, cultured by using Neural Differentiation Medium A from day 1, and then cultured by using Neural Differentiation Medium B from day 7.

In the present disclosure, the Neural Differentiation Medium A comprises one or more of retinoic acid, BDNF (brain-derived neurotrophic factor), GDNF (glial cell-derived neurotrophic factor), ascorbic acid, nutritional supplement, Neurobasal medium and B-27 Supplement Minus Vitamin A. The Neural Differentiation Medium B comprises one or more of BDNF, GDNF, ascorbic acid, nutritional supplement, Neurobasal medium, and B-27 Supplement Minus Vitamin A.

In the present disclosure, addition of the nutritional supplement to the neural medium can accelerate differentiation and maturation of the neural cells. In the present disclosure, the nutritional supplement is one or more selected from a group consisting of SU5402, BIBF1120, IBMX, and glucose.

SU5402 and BIBF1120 are used to inhibit FGF and VEGF receptor signaling pathways, inhibit cell aggregation, and promote migration of immature neurons, allowing neurons to have sufficient space to facilitate the growth of neurites and further maturation into truly functional neurons. The aggregation of cells can lead to a high density of neurons, which makes cells lose opportunity to extend the neurites, which is adverse to cell maturation. The existing differentiation and culture methods of neurons generally have problems of adversely affecting cell health, maturation, and homogeneity, and even mass mortality before maturity due to aggregation of neural cells. Adding SU5402 and BIBF1120 can effectively prevent these situations by reducing cell aggregation, allowing a quick maturation of neural cells, while maintaining a healthy and uniform density, and reducing mortality, so as to meet the needs of a larger scale and functions in scientific research and industry, and to be applicable to high-throughput screening. Moreover, neural cells cultured by using a medium supplemented with SU5402 and BIBF1120 can be maintained for more than 3 years, but neural cells generated by a different method for differentiating human neural stem cells can only grow in vitro for 1-2 month until massive death occurs.

IBMX is a non-specific inhibitor of intracellular cAMP degrading enzyme-phosphodiesterase (PDE), which can increase the level of intracellular cAMP by inhibiting the degradation of cAMP. The role of IBMX requires the participation of glucose to exert its effects. The differentiation and maturation of neurons require a large amount of cAMP to provide energy, rendering a large consumption of cAMP and a relatively high cost. IBMX can increase the concentration of intracellular cAMP indirectly by inhibiting the activity of cAMP degrading enzyme-phosphodiesterase. The use of IBMX and glucose to replace a large amount of cAMP not only allows for a quicker maturation of neural cells, but also reduces the cost of cell culture, which meets the needs of a larger scale and functions in scientific research and industry, and is suitable for high-throughput screening.

The present disclosure also provides a medium for inducing differentiation into functional cerebral cortical cells, comprising neural medium and nutritional supplement.

In one embodiment, the nutritional supplement comprises one or more of SU5402, BIBF1120, IBMX, and glucose.

In one embodiment, the nutritional supplement comprises SU5402.

In one embodiment, the nutritional supplement comprises one or more of 100 nM~100 μM SU5402, 1~500 ng/mL BIBF1120, 1~100 μM IBMX and 1~10 mM glucose.

In one embodiment, the nutritional supplement comprises 100 nM~100 μM SU5402, 1~500 ng/mL BIBF1120, 1~100 μM IBMX and 1~10 mM glucose.

In one embodiment, the nutritional supplement comprises 80~120 nM SU5402, 150~250 ng/mL BIBF1120, 5~15 μM IBMX, and 3~8 mM glucose.

In one embodiment, the nutritional supplement comprises 100 nM SU 5402, 200 ng/mL BIBF 1120, 10 μM IBMX and 5 mM glucose.

In the present disclosure, the neural medium is chosen from brain neural medium, and a combination of different factors can be optionally added. In one embodiment, the neural medium comprises retinoic acid, BDNF, GDNF, ascorbic acid, Neurobasal medium, and B-27 Supplement Minus Vitamin A; in one embodiment, the neural medium comprises BDNF, GDNF, ascorbic acid, Neurobasal medium, and B-27 Supplement Minus Vitamin A.

In the induced differentiation of neural stem cells or neural progenitor cells, culture is conducted by using Neural Differentiation Medium A from day 1, and culture is continued by using Neural Differentiation Medium B from day 7.

Specifically, the Neural Differentiation Medium A comprises Neural Medium A and nutritional supplement. The Neural Medium A comprises retinoic acid, BDNF, GDNF, ascorbic acid, Neurobasal medium and B-27 Supplement Minus Vitamin A. In one embodiment, the Neural Differentiation Medium A comprises 2 μM retinoic acid, 20 ng/mL BDNF, 20 ng/mL GDNF, 0.2 mM ascorbic acid, 100 nM SU 5402, 200 ng/mL BIBF 1120, 10 μM IBMX, 5 mM glucose, the Neurobasal medium and the B-27 Supplement Minus Vitamin A, wherein the ratio of Neurobasal medium to the B-27 Supplement is 50:1 (Unless otherwise specified, the "ratio" in the context of the present disclosure means "mass ratio").

Specifically, the Neural Differentiation Medium B comprises Neural Medium B and nutritional supplement. The Neural Medium B comprises BDNF, GDNF, ascorbic acid, Neurobasal medium and B-27 Supplement Minus Vitamin A In one embodiment, the Neural Differentiation Medium B comprises 20 ng/mL BDNF, 20 ng/mL GDNF, 0.2 mM ascorbic acid, 100 nM SU5402, 200 ng/mL BIBF1120, 10 μM IBMX, 5 mM glucose, the Neurobasal medium and the B-27 Supplement Minus Vitamin A, wherein the ratio of Neurobasal medium to B-27 Supplement Minus Vitamin A is 50:1.

In the present disclosure, the Neural Differentiation Medium A is used for culturing at 37° C., 5% $CO_2$ in the cell culture incubator starting from day 1, with half of the medium being replaced every 3 to 5 days; and the Neural Differentiation Medium B is used starting from day 7 to continue the culturing at 37° C., 5% $CO_2$ in the cell culture incubator, with half of the medium being replaced every 3~5 days. Starting from day 7, the maturity degree of the neural cells can be detected by methods such as electrophysiological and immunofluorescence staining, and become ready to use when a target functional index is realized.

In the present disclosure, specific factors such as an inhibitor of FGF signaling pathway, an inhibitor of VEGF signaling pathway, and/or an activator of cAMP, are added at specific time points during the induced differentiation of neural stem cells or neural progenitor cells into various neural cells to accelerate the differentiation and maturation of neural cells, enabling the generation of stable and healthy neural cells with major functions, including excitatory and inhibitory neurons, at about 7~14 days after the initiation of the induced differentiation from human neural progenitor cells, so that human neural cells grown in vitro can be truly applied in the fields such as drug screening, with reduced manufacturing cost and shortened production time. In addition, the ingredients of the media included in the method provided by the present disclosure are serum-free and animal origin-free agents, and therefore are also suitable for clinical transplantation trials.

DESCRIPTION OF THE DRAWINGS

In order to illustrate the embodiments of the present disclosure or the technical solutions of the prior art more clearly, the drawings as needed for the description of the embodiments or the prior art will be briefly introduced below. Obviously, the drawings in the following description only relates to examples of the present disclosure. Other drawings can also be contemplated by a person having ordinary skills in the art from the provided drawings of the present disclosure without any creative efforts.

DETAILED DESCRIPTION OF EMBODIMENTS

The technical solutions in the examples of the present disclosure will be described explicitly and comprehensively hereinafter. Obviously, only a part of the embodiments of the present disclosure is described herein. All other embodiments obtainable by one with ordinary skills in the art based on the examples of the present disclosure without making any creative efforts are within the protection scope of the present disclosure.

Example 1

Step 1: The neural progenitor cells (hNPCs) generated by differentiation from human induced pluripotent stem cell line DYR0100 were dissociated by accutase, and then plated on poly-D-lysine/laminin-coated plate at a density of $5 \times 10^5/cm^2$.

Step 2: Starting from day 1, culturing was conducted by using Neural Differentiation Medium A at 37° C., 5% $CO_2$ in the cell culture incubator for 7 days, with half of the medium being replaced every 3 days. The Neural Differentiation Medium A comprised in final concentrations of 2 µM retinoic acid, 20 ng/mL BDNF, 20 ng/mL GDNF, 0.2 mM ascorbic acid, 100 nM SU5402, 200 ng/mL BIBF 1120, 10 µM IBMX, and 5 mM glucose in the Neurobasal medium and the B-27 Supplement Minus Vitamin A, wherein the ratio of the Neurobasal medium to B-27 Supplement Minus Vitamin A was 50:1.

Step 3: Starting from day 7, the culturing was conducted by using Neural Differentiation Medium B at 37° C., 5% $CO_2$ in the cell culture incubator, with half of the medium being replaced every 3 days. The Neural Differentiation Medium B comprised in final concentrations of 20 ng/mL BDNF, 20 ng/mL GDNF, 0.2 mM ascorbic acid, 100 nM SU5402, 200 ng/mL BIBF1120, 10 µM IBMX, and 5 mM glucose in the Neurobasal medium and the B-27 Supplement Minus Vitamin A, wherein the ratio of Neurobasal medium to B-27 Supplement Minus Vitamin A was 50:1. Starting from day 7, the maturity-level of the neural cells could be measured by methods such as electrophysiological and immunofluorescence staining, and became ready to use when the predetermined functional index was realized.

Figure 1:
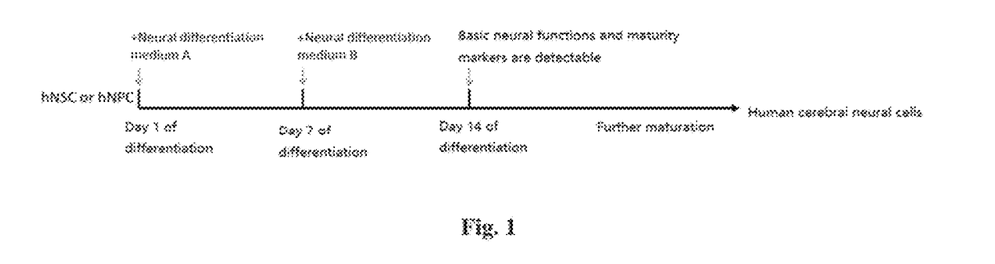
FIG. 1 is the schematic flow diagram of the method provided in the present disclosure for inducing differentiation into functional cerebral cortical cells.

Referring to FIG. 1, which is a schematic flow diagram of the method provided by the present disclosure for inducing differentiation into functional cerebral cortical cells, hNSCs or hNPCs were subjected to induced differentiation after being dissociated; the Neural Differentiation Medium A was used from starting day 1 of the induced differentiation; the Neural Differentiation Medium B was used starting from day 7; basic neural functions and maturation markers became detectable from day 14; and human cerebral cortical neural cells could be generated after further maturation. Specifically, the Neural Differentiation Medium A comprised in final concentrations of 2 µM retinoic acid, 20 ng/mL BDNF, 20 ng/mL GDNF, 0.2 mM ascorbic acid, 100 nM SU5402, 200 ng/mL BIBF1120, 10 µM IBMX, 5 mM glucose in the Neurobasal and B-27 (Minus Vitamin A) medium; the Neural Differentiation Medium B comprised in final concentrations of 20 ng/mL BDNF, 20 ng/mL GDNF, 0.2 mM ascorbic acid, 100 nM SU5402, 200 ng/mL BIBF1120, 10 µM IBMX, and 5 mM glucose, in the Neurobasal and B-27 (Minus Vitamin A) medium.

Figure 2:
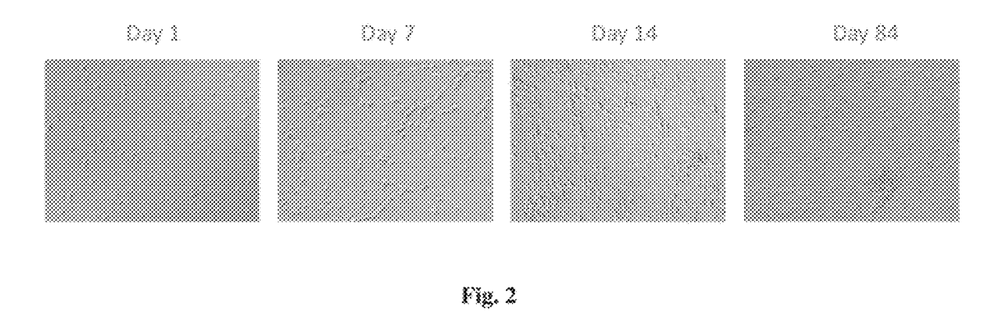
FIG. 2 shows the bright-field photos of human neural cells on day 1, 7, 14, and 84 of the induced differentiation of Example 1.
Figure 3:
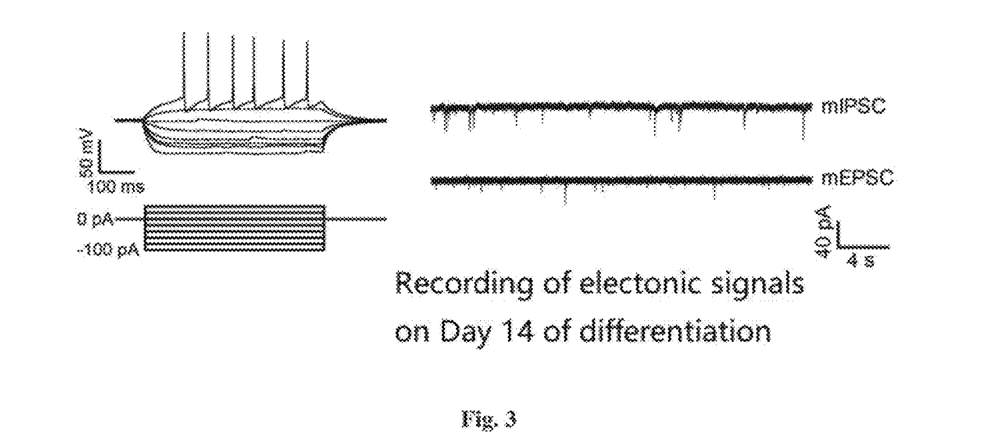
FIG. 3 shows examples of action potentials of human neural cells recorded by single-cell patch clamp, examples of miniIPSC (inhibitory neural firing) and miniEPSC (excitatory neural firing) on day 14 of the induced differentiation of Example 1.
Figure 4:
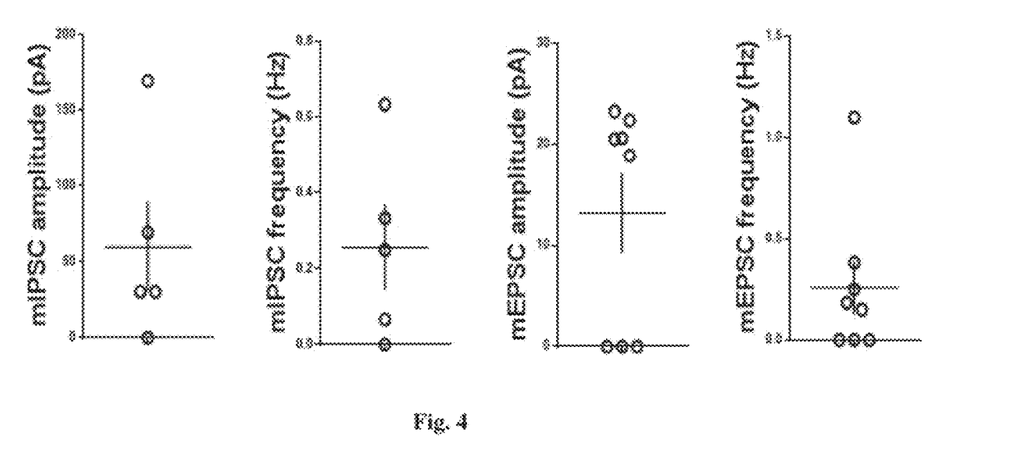
FIG. 4 shows the statistical data of the amplitude and frequency of the excitatory and inhibitory neural firing of the cells, which were recorded on day 14 of the induced differentiation of Example 1.

Referring to FIG. 2, FIG. 3 and FIG. 4, FIG. 2 shows the bright-field photos of human neural cells on day 1, 7, 14, and 84 of the induced differentiation of Example 1; FIG. 3 shows examples of action potentials of human neural cells recorded by single-cell patch clamp, examples of mIPSCs (inhibitory neural firing) and mEPSCs (excitatory neural firing) on day 14 of the induced differentiation of Example 1; FIG. 4 shows the statistical data of the amplitude and frequency of the excitatory and inhibitory firing of the cells, which were recorded on day 14 of the induced differentiation of Example 1. As shown in FIG. 2, FIG. 3 and FIG. 4, the neural cells including excitatory and inhibitory neurons with electrophysiological functions and could be subjected to long-term culturing became obtainable on day 14 by using the method of the present disclosure.

Comparative Example 1

Different from Example 1, a common neural medium (Neurobasal medium+B-27) was used instead of the Neural Differentiation Medium A and Neural Differentiation Medium B.

Comparative Example 2

Different from Example 1, a medium promoting the neurophysiological maturity of neural cells (BrainPhys) manufactured by a Canadian company well-known for stem cell reagents (CompA) was used instead of the Neural Differentiation Medium A and Neural Differentiation Medium B.

Comparative Example 3

Different from Example 1, a medium supplement promoting the maturity of neural cells by BrainXell (CompB), a company run by a well-known American professor in the field of stem cell neural differentiation, was used instead of the Neural Differentiation Medium A and Neural Differentiation Medium B.

Figure 5:
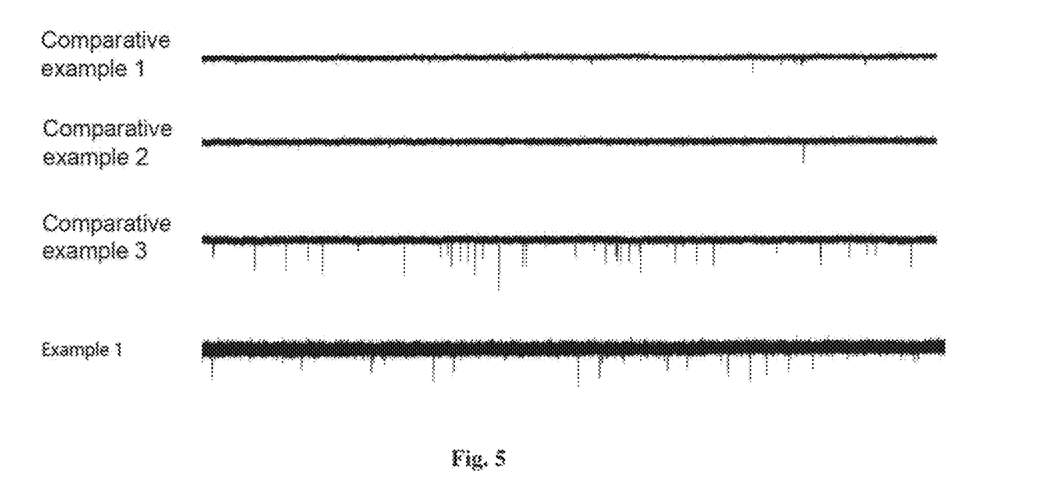
FIG. 5 shows an exemplified record of sEPSC (spontaneous excitatory neural firing) of human neural cells recorded by single cell patch clamp on day 14 of the induced differentiation.
Figure 6:
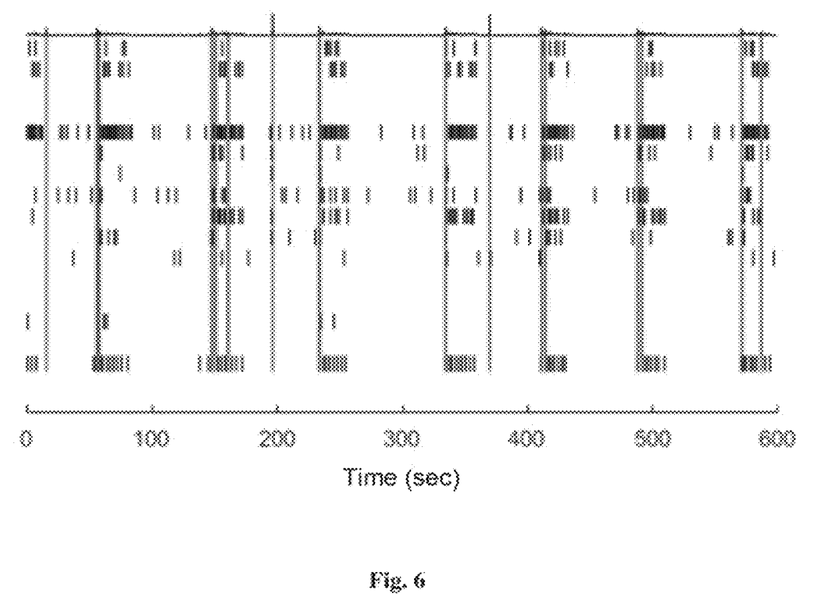
FIG. 6 shows an exemplified record of spontaneous neural firing of human neural cells on day 14 of the induced differentiation of Example 1.

Referring to FIG. 5 and FIG. 6, FIG. 5 shows an exemplified record of sEPSC (spontaneous excitatory neural firing) of human neural cells recorded by single cell patch clamp on day 14 of the induced differentiation, in which Comparative Example 1, Comparative Example 2, Comparative Example 3 and Example 1 are shown from top to bottom sequentially. FIG. 6 shows an exemplified record of spontaneous neural firing of human neural cells on day 14 of the induced differentiation of Example 1 (recorded by MEA (Multi Electrode Array), Axion Bioscience). It can be seen that the association of clustered action potential firings between multiple electrodes was found through software analysis. This represents that on day 14 certain network connections (a representation of a more mature function) were formed by the neural cells generated by the differentiation method provided in Example 1. However, the same phenomenon was not observed on neural cells generated by other differentiation methods (Day 14). Also, according to the reported literatures, such a phenomenon can hardly be observed on any human neural cells generated by culturing with other differentiation methods or media even in 2 months of differentiation.

Figure 7:
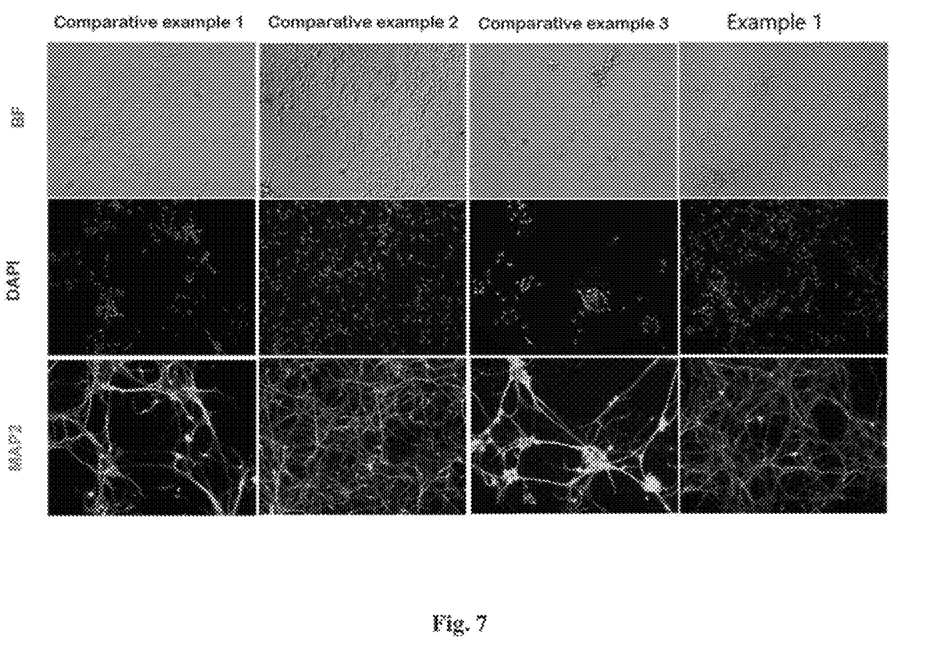
FIG. 7 shows the results of immunofluorescence staining of MAP2 on day 14 of the differentiation.
Figure 8:
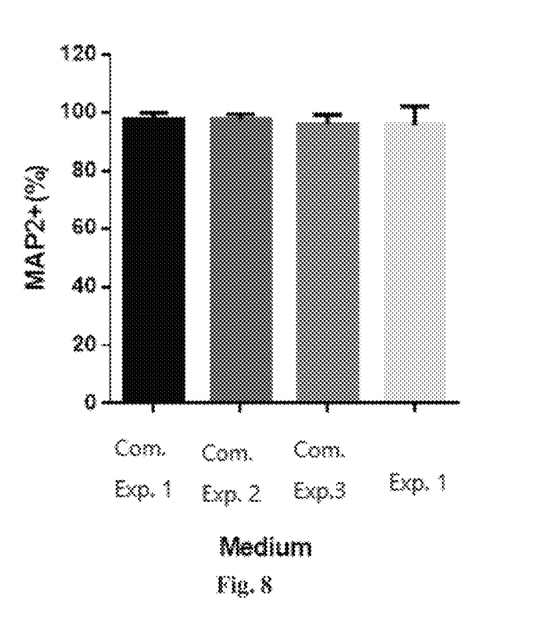
FIG. 8 is a histogram showing the results of immunofluorescence staining of MAP2 on day 14 of the differentiation.

Referring to FIG. 7 and FIG. 8, FIG. 7 shows the results of immunofluorescence staining of MAP2 on day 14 of the differentiation of Example 1 and Comparative Examples 1~3, of which Comparative Example 1, Comparative Example 2, Comparative Example 3, and Example 1 are shown from left to right, respectively; and bright-field photos, DAPI staining results, and MAP2 staining results are shown from top to bottom, respectively. FIG. 8 is a histogram showing the results of immunofluorescence staining of MAP2 on day 14 of the differentiation of Comparative examples 1~3 and Example 1, of which Comparative Example 1, Comparative Example 2, Comparative Example 3, and Example 1 are shown from left to right.

Figure 9:
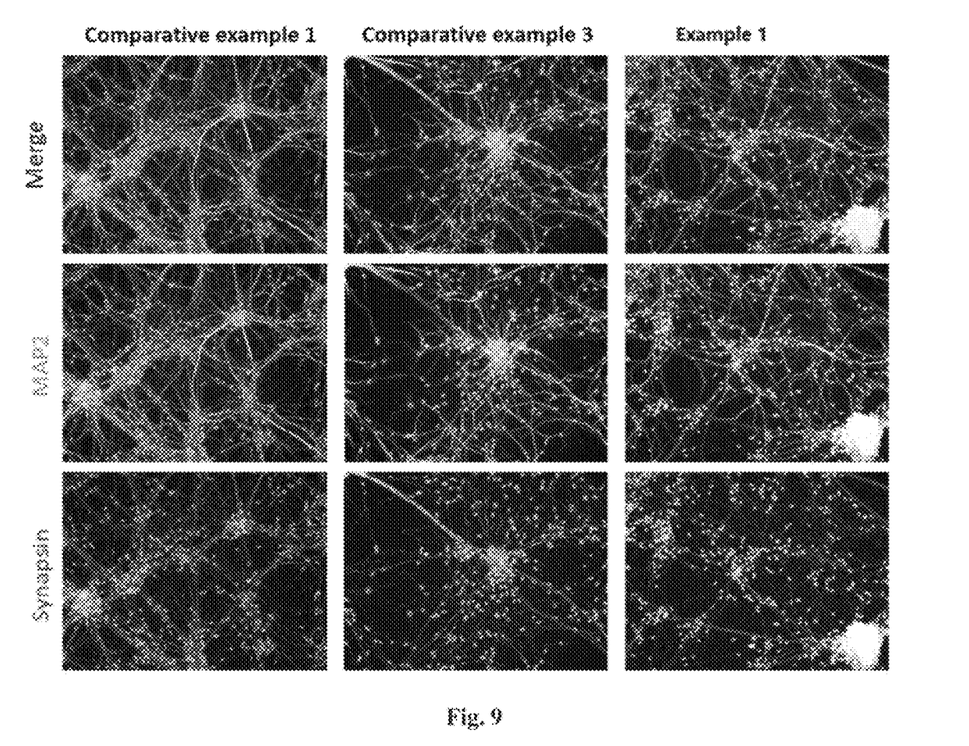
FIG. 9 shows the results of immunofluorescence staining of Synapsin on day 14 of the differentiation.
Figure 10:
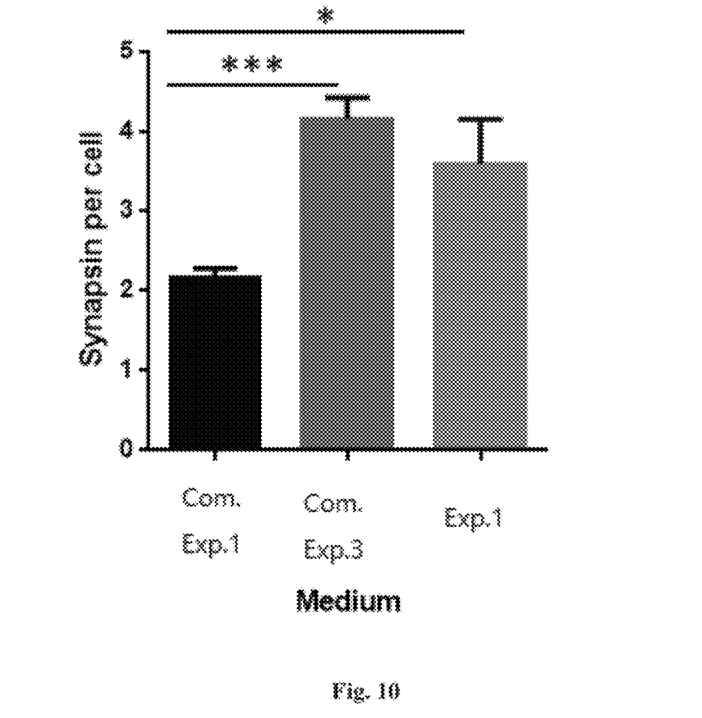
FIG. 10 is a histogram showing the results of immunofluorescence staining of Synapsin on day 14 of the differentiation.

Referring to FIG. 9 and FIG. 10, FIG. 9 shows the results of immunofluorescence staining of Synapsin on day 14 of the differentiation of Comparative Examples 1~3 and Example 1, of which Comparative Example 1, Comparative Example 3, and Example 1 are shown from left to right, respectively, and the Merged results, MAP2 staining results and Synapsin staining results are shown from top to bottom, respectively. FIG. 10 is a histogram showing the results of immunofluorescence staining of Synapsin on day 14 of the differentiation of Example 1 and Comparative Examples 1~3, of which Comparative Example 1, Comparative Example 3, and Example 1 are shown from left to right, respectively.

Figure 11:
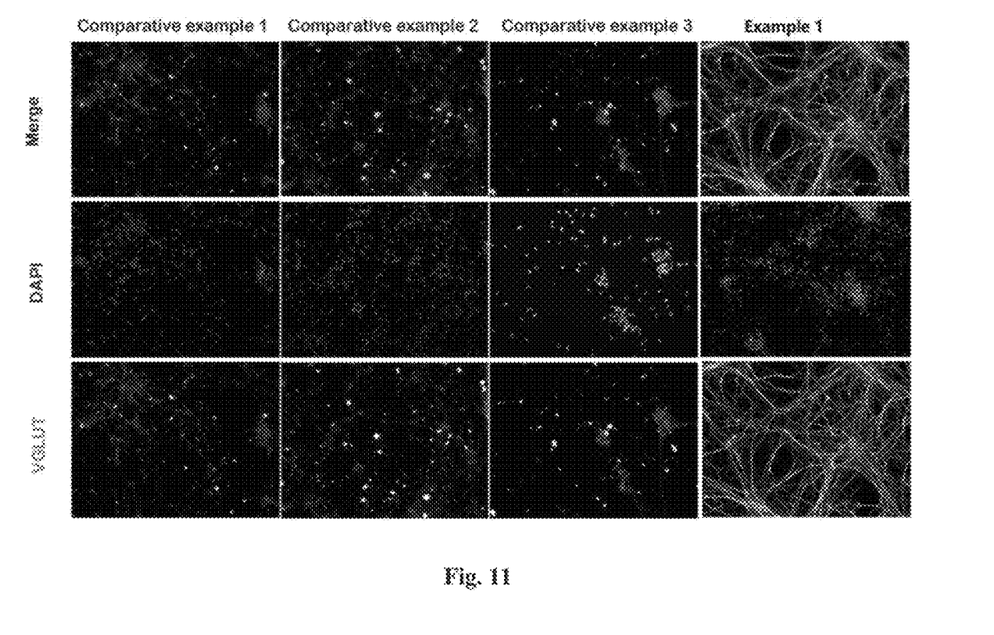
FIG. 11 shows the results of immunofluorescence staining of vGlut on day 21 of the differentiation.
Figure 12:
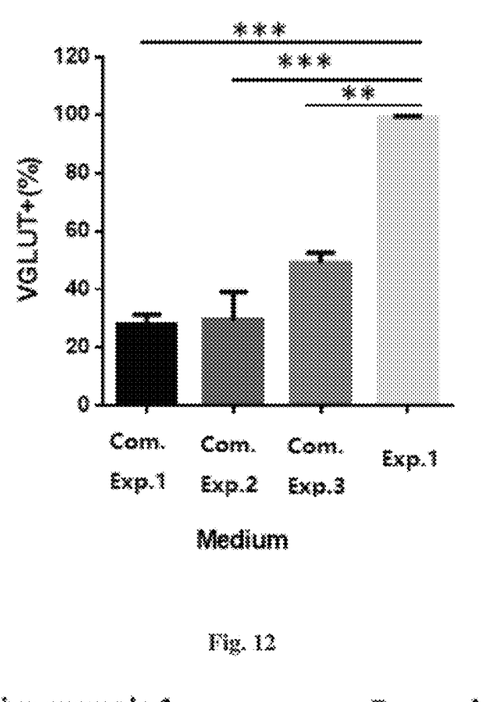
FIG. 12 is a histogram showing the results of immunofluorescence staining of vGlut on day 21 of the differentiation.

Referring to FIG. 11 and FIG. 12, FIG. 11 shows the results of immunofluorescence staining of vGlut on day 21 of the differentiation of Example 1 and Comparative Examples 1~3, of which Comparative Example 1, Comparative Example 2, Comparative Example 3, and Example 1 are shown from left to right, respectively, and the Merge results, DAPI staining images and vGlut staining images are shown from top to bottom, respectively. FIG. 12 a histogram showing the results of immunofluorescence staining of vGlut on day 21 of the differentiation of Example 1 and Comparative Examples 1~3, of which Comparative Example 1, Comparative Example 2, Comparative Example 3, and Example 1 are shown from left to right, respectively.

It can be known from FIG. 7~FIG. 12 that neural cells including excitatory and inhibitory neurons can be fast generated by the method provided in the present disclosure.

Example 2

Step 1: the neural progenitor cells (hNPCs) generated by differentiation from human induced pluripotent stem cell line DYR0100 were dissociated by accutase, and then plated on a poly-D-lysine/laminin-coated plate at a density of $5 \times 10^5/cm^2$.

Step 2: Starting from day 1, culturing was conducted by using Neural Differentiation Medium A at 37° C., 5% $CO_2$ in the cell culture incubator for 7 days, with half of the medium being replaced every 3 days. The Neural Differentiation Medium A comprised in final concentrations of 2 μM retinoic acid, 20 ng/mL BDNF, 20 ng/mL GDNF, 0.2 mM ascorbic acid, 10 μM SU5402 in Neurobasal medium and B-27 Supplement Minus Vitamin A, wherein the ratio of the Neurobasal medium to B-27 Supplement was 50:1.

Step 3: Starting from day 7, the culturing was conducted by using Neural Differentiation Medium B at 37° C., 5% $CO_2$ in the cell culture incubator, with half of the medium being replaced every 3 days. The Neural differentiation medium B comprised in final concentrations of 20 ng/mL BDNF, 20 ng/mL GDNF, 0.2 mM ascorbic acid, 10 μM SU5402 in the Neurobasal medium and B-27 Supplement (Minus Vitamin A), wherein the ratio of the Neurobasal medium to the B-27 Supplement was 50:1. Starting from day 7, the maturity-level of the neural cells could be measured by methods such as electrophysiological and immunofluorescence staining, and became ready to use when the predetermined functional index was realized.

Figure 13:
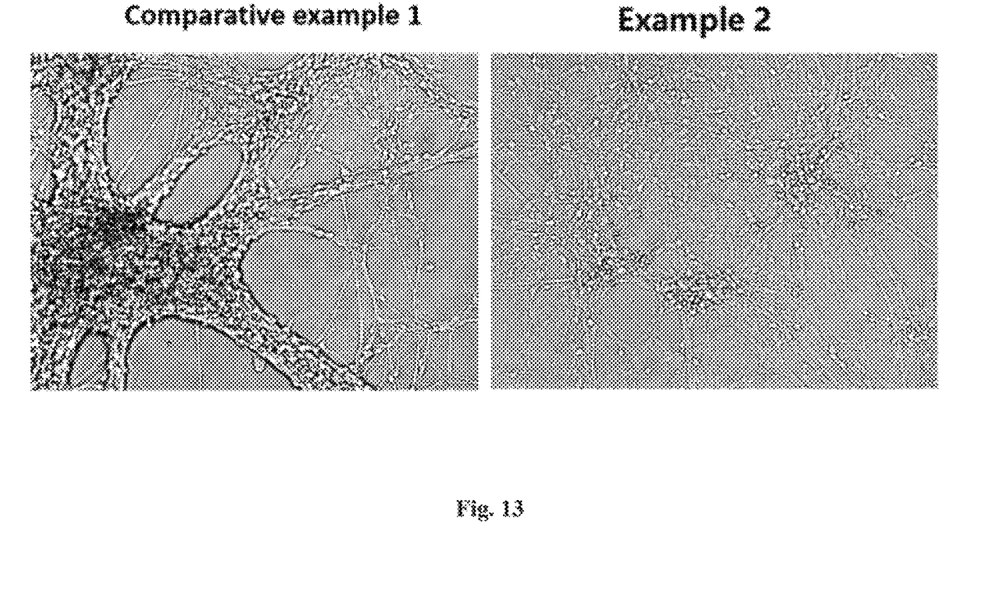
FIG. 13 is the bright-field photos of human neural cells on day 21 of the differentiation of Example 2 and Comparative Example 1.
Figure 14:
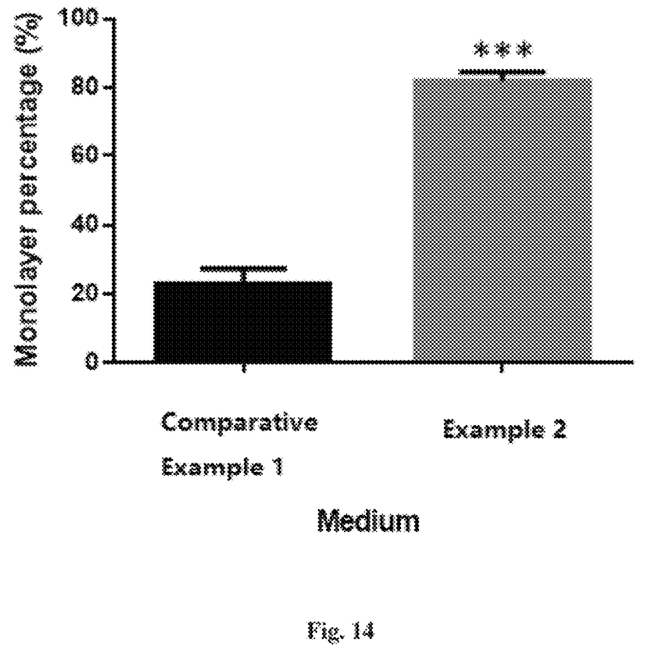
FIG. 14 is a histogram showing the statistical results of dispersion degree of human neural cells on day 21 of the differentiation of Example 2 and Comparative Example 1.

Referring to FIG. 13~FIG. 14, FIG. 13 is the bright-field images of the human neural cells on day 21 of the induced differentiation of Example 2 and Comparative Example 1; FIG. 14 is the statistical results of dispersion degree of the cells on day 21 of the induced differentiation of Example 2 and Comparative Example 1.

Figure 15:
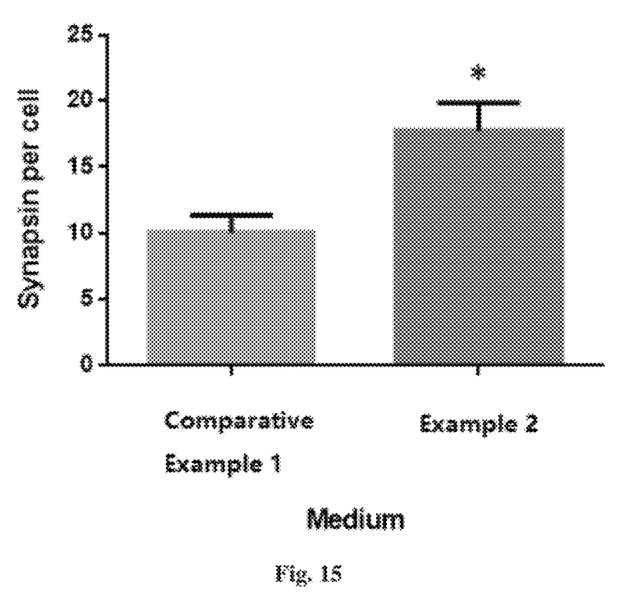
FIG. 15 is a histogram showing the results of immunofluorescence staining of Synapsin on day 21 of the differentiation of Example 2 and Comparative Example 1.
Figure 16:
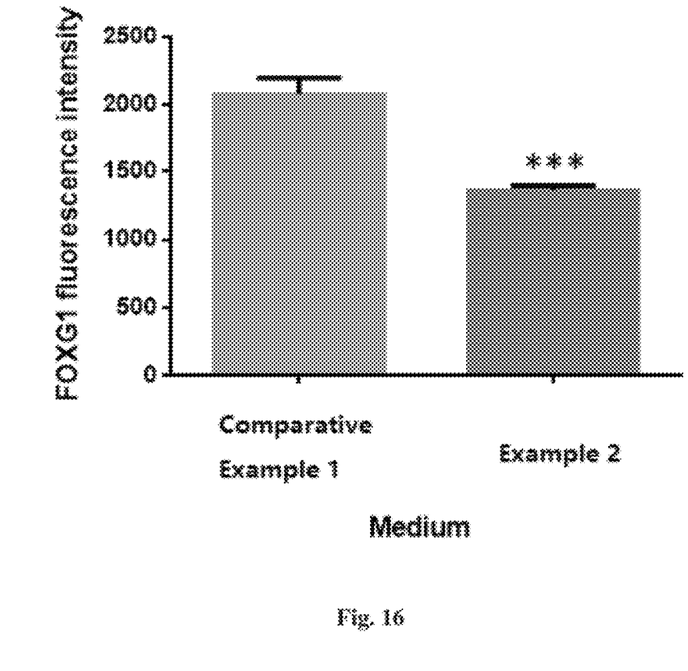
FIG. 16 is a histogram showing the results of immunofluorescence staining of FOXG1 on day 21 of the differentiation of Example 2 and Comparative Example 1.

Referring to FIG. 15~FIG. 16, FIG. 15 is a histogram showing the results of immunofluorescence staining of Synapsin on day 21 of the differentiation of Example 2 and Comparative Example 1. FIG. 16 is histogram showing the results of immunofluorescence staining of FOXG1 on day 21 of the differentiation of Example 2 and Comparative Example 1.

Figure 17:
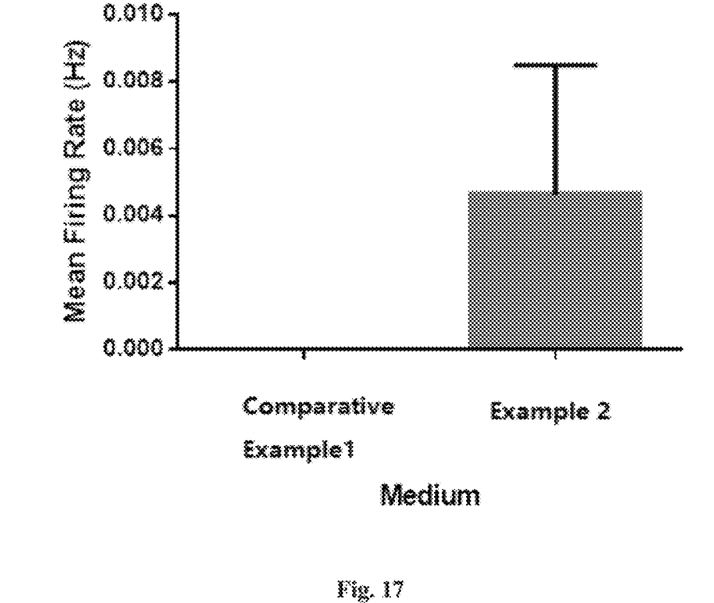
FIG. 17 is a statistic graph showing the record of spontaneous neural firing of human neural cells on day 7 of the differentiation of Example 2 and Comparative Example 1.

Referring to FIG. 17, FIG. 17 is the statistic results of the spontaneous neural firing records of the human neural cells on day 7 of the differentiation in Example 2 and Comparative Example 1 (recorded by MEA, Axion Bioscience). No electrophysiological signal was detected on day 7 for the cells in the Neural medium.

It can be known from FIG. 13~FIG. 17, the method provided by the present disclosure can inhibit cell aggregation and facilitate maturation of neurons, such that the neural cells are sufficiently spaced, which is favorable for the growth of neurites and for further maturation into functional neurons.

Example 3

Step 1: The neural progenitor cells (hNPCs) generated by differentiation from human induced pluripotent stem cell line DYR0100 were dissociated by accutase, and then plated on a poly-D-lysine/laminin-coated plate at a density of $5 \times 10^5/cm^2$.

Step 2: Starting from day 1, culturing was conducted by using Neural Differentiation Medium A at 37° C., 5% $CO_2$ in the cell culture incubator for 7 days, with half of the medium being replaced every 3 days. The Neural Differentiation Medium A comprised in final concentrations of 2 μM retinoic acid, 20 ng/mL BDNF, 20 ng/mL GDNF, 0.2 mM ascorbic acid, 5 μM SU5402, and 50 μM IBMX in Neurobasal medium and B-27 Supplement Minus Vitamin A, wherein the ratio of the Neurobasal medium to B-27 Supplement was 50:1.

Step 3: Starting from day 7, the culturing was conducted by using Neural Differentiation Medium B at 37° C., 5% $CO_2$ in the cell culture incubator, with half of the medium being replaced every 3 days. The Neural differentiation medium B comprised in final concentrations of 20 ng/mL BDNF, 20 ng/mL GDNF, 0.2 mM ascorbic acid, 5 μM SU5402 and 50 μM IBMX in Neurobasal medium and B-27 Supplement (Minus Vitamin A), wherein the ratio of the Neurobasal medium to the B-27 Supplement was 50:1. The results showed that the method provided in Example 3 could effectively inhibit cell aggregation in comparison with Comparative Example 1, Comparative Example 2, and Comparative Example 3.

Example 4

Step 1: The neural progenitor cells (hNPC) generated by differentiation from human induced pluripotent stem cell line DYR0100 were dissociated by accutase, and then plated on a poly-D-lysine/laminin-coated plate at a density of $5 \times 10^5/cm^2$.

Step 2: Starting from day 1, culturing was conducted by using Neural Differentiation Medium A at 37° C., 5% $CO_2$ in the cell culture incubator for 7 days, with half of the medium being replaced every 3 days. The Neural Differentiation Medium A comprised in final concentrations of 2 μM retinoic acid, 20 ng/mL BDNF, 20 ng/mL GDNF, 0.2 mM ascorbic acid, 5 ng/mL BIBF1120, and 50 μM IBMX in Neurobasal medium and B-27 Supplement Minus Vitamin A, wherein the ratio of the Neurobasal medium to the B-27 Supplement was 50:1.

Step 3: Starting from day 7, the culturing was conducted by using Neural Differentiation Medium B at 37° C., 5% $CO_2$ in the cell culture incubator, with half of the medium being replaced every 3 days. The Neural differentiation medium B comprised in final concentrations of 20 ng/mL BDNF, 20 ng/mL GDNF, 0.2 mM ascorbic acid, 5 ng/mL BIBF1120, and 50 μM IBMX in Neurobasal medium and B-27 Supplement (Minus Vitamin A), wherein the ratio of the Neurobasal medium to B-27 Supplement was 50:1. The results showed that the method provided in Example 3 could effectively inhibit cell aggregation in comparison with Comparative Example 1, Comparative Example 2, and Comparative Example 3.

The above described examples are only preferred embodiments of the present invention. It should be pointed out that for persons with ordinary skills in the art, improvements and embellishments can be made without departing from the sprits of the present disclosure, and these improvements and embellishments shall also be regarded as within the scope of protection of the present disclosure.

The invention claimed is:

1. A medium for inducing differentiation of neural stem cells or neural progenitor cells into functional cerebral cortical cells, comprising a neural medium and a nutritional supplement, wherein the nutritional supplement comprises 80 nM to 100 μM SU5402, 150 to 250 ng/mL BIBF1120, 1 to 100 μM IBMX, and 1 to 10 mM glucose.

2. The medium according to claim 1, wherein the nutritional supplement comprises 80 to 120 nM SU5402.

3. The medium according to claim 1, wherein the nutritional supplement comprises 100 nM SU5402, 200 ng/ml BIBF1120, 10 μM IBMX, and 5 mM glucose.

4. The medium according to claim 1, wherein the nutritional supplement comprises 80 nM to 10 μM SU5402, 150 to 250 ng/ml BIBF1120, 5 to 15 μM IBMX, and 3 to 8 mM glucose.

5. The medium according to claim 1, wherein the nutritional supplement comprises 10 μM SU5402.

6. The medium according to claim 1, wherein the nutritional supplement comprises 5 μM SU5402 and 50 μM IBMX.

7. A method for inducing differentiation of neural stem cells or neural progenitor cells into functional cerebral cortical cells, comprising:
   disassociating neural stem cells or neural progenitor cells,
   inoculating said neural stem cells or neural progenitor cells on a cell culture plate after being dissociated,
   culturing said neural stem cells or neural progenitor cells in Neural Differentiation Medium A from day 1, and then
   culturing said neural stem cells or neural progenitor cells in Neuronal Differentiation Medium B from day 7;
   wherein
   the Neural Differentiation Medium A comprises retinoic acid, BDNF, GDNF, ascorbic acid, a nutritional supplement, Neurobasal medium, and a media supplement minus Vitamin A;
   the Neural Differentiation Medium B comprises BDNF, GDNF, ascorbic acid, the nutritional supplement, Neurobasal medium, and the media supplement minus Vitamin A; and
   the nutritional supplement comprises 80 nM to 100 μM SU5402, 150 to 250 ng/mL BIBF1120, 1 to 100 μM IBMX, and 1 to 10 mM glucose.

8. The method according to claim 7, wherein the nutritional supplement comprises 80 to 120 nM SU5402.

9. The method according to claim 7, wherein the nutritional supplement comprises 100 nM SU5402, 200 ng/ml BIBF1120, 10 μM IBMX and 5 mM glucose.

10. The method according to claim 7, wherein
the Neural Differentiation Medium A comprises 2 μM retinoic acid, 20 ng/ml BDNF, 20 ng/ml GDNF, 0.2 mM ascorbic acid, 100 nM SU5402, 200 ng/ml BIBF1120, 10 μM IBMX, 5 mM glucose, the Neurobasal medium and the media supplement minus Vitamin A is 50:1; and
the Neural Differentiation Medium B comprises 20 ng/ml BDNF, 20 ng/ml GDNF, 0.2 mM ascorbic acid, 100 nM SU5402, 200 ng/ml BIBF1120, 10 μM IBMX, 5 mM glucose, the Neurobasal medium and the media supplement minus Vitamin A, wherein the ratio of the Neurobasal medium to the media supplement minus Vitamin A is 50:1.

11. The method according to claim 10, wherein the culturing is conducted in the Neural Differentiation Medium A from day 1, with half of the Neural Differentiation Medium A being replaced every 3 to 5 days; and wherein the culturing is continued by using the Neural Differentiation Medium B starting from day 7, with half of the Neural Differentiation Medium B being exchanged every 3 to 5 days.

12. The method according to claim 11, wherein the disassociating comprises contacting the neural stem cells or neural progenitor cells with accutase and then plating the neural stem cells or neural progenitor cells on a poly-D-lysine/laminin-coated plate at a density of $5\times10^5/cm^2$.

13. The method according to claim 7, wherein the nutritional supplement comprises 80 nM to 10 μM SU5402, 150 to 250 ng/mL BIBF1120, 5 to 15 μM IBMX and 3 to 8 mM glucose.

14. The method according to claim 7, wherein the nutritional supplement comprises 10 μM SU5402.

15. The method according to claim 7, wherein the nutritional supplement comprises 5 μM SU5402 and 50 μM IBMX.

* * * * *